United States Patent [19]
Aldridge et al.

[11] Patent Number: 5,859,703
[45] Date of Patent: Jan. 12, 1999

[54] SPECTROPHOTOMETRIC ANALYSIS

[75] Inventors: Paul K. Aldridge, Ledyard, Conn.; Stephen V. Hammond; Tony G. Axon, both of Sandwich, United Kingdom

[73] Assignee: Pfizer Inc., New York, N.Y.

[21] Appl. No.: 857,919

[22] Filed: May 16, 1997

[30] Foreign Application Priority Data

May 17, 1996 [GB] United Kingdom ............... 96 10 344

[51] Int. Cl.[6] ................................ G01J 3/02; G01J 3/42
[52] U.S. Cl. ..................... 356/319; 356/326; 356/446; 250/339.11
[58] Field of Search .................... 356/319, 326, 356/328, 445, 446; 250/339.11

[56] References Cited

U.S. PATENT DOCUMENTS

| | | | |
|---|---|---|---|
| 2,311,101 | 2/1943 | Tuttle et al. | 356/446 |
| 4,073,590 | 2/1978 | Brown | 356/446 |
| 5,478,750 | 12/1995 | Bernstein et al. | 436/164 |

FOREIGN PATENT DOCUMENTS

| | | |
|---|---|---|
| 0068717 | 1/1983 | European Pat. Off. . |
| 0388168 | 9/1990 | European Pat. Off. . |
| 0495569 | 7/1992 | European Pat. Off. . |
| 0640826 | 3/1995 | European Pat. Off. . |
| 0807811 | 3/1998 | European Pat. Off. . |
| 3030879 | 2/1981 | Germany . |
| 2292798 | 3/1996 | United Kingdom . |

OTHER PUBLICATIONS

Abstract of JP 61–34428.
Abstract of JP 62–28622.
Abstract of JP 63–172931.
Abstract of JP 06–011440.

*Primary Examiner*—F. L. Evans
*Attorney, Agent, or Firm*—Peter C. Richardson; Gregg C. Benson; Jennifer A. Kispert

[57] ABSTRACT

The present invention relates to an apparatus for spectrophotometric analysis of a material in a container by reflectance of a beam applied to the material through an aperture in a primary mask. A restricted beam resulting from the primary mask is applied through a port in an opaque secondary mask to the material. The restricted beam is wholly within the port and radiation reflected from the material passes through the port to detectors for analysis. The secondary mask defines by its port an area on the base of the container through which the restricted beam is applied to the material and is not subjected to spurious reflections and refractions otherwise created by the container between its base and side wall. The container may be spaced from the secondary mask and inclined relative thereto so that the secondary mask shields the top and bottom ends of the container.

The present invention also relates to a conversion kit with primary and secondary masks for fitting to existing spectrophotometers and an apparatus by which an array of containers can be fed successively and automatically to overlie the port for analysis and thereafter removed.

28 Claims, 5 Drawing Sheets

SPECTROPHOTOMETRIC ANALYSIS

TECHNICAL FIELD & BACKGROUND ART

The present invention relates to spectrophotometric analysis and is particularly concerned with apparatus for analysis of a sample material, typically in powder or liquid form, by reflectance measurements resulting from a beam of electromagnetic radiation (usually near infrared) applied to the material.

Spectrophotometers are well known to provide quantitive and qualitative analysis of substances and materials and are used extensively within the chemical, petro-chemical, food, agriculture and pharmaceutical industries. Typical infrared reflectance spectrophotometers are sold under the Trade Marks "COMPSCAN" by the Gardner Neotec Division of Pacific Scientific and "MODEL 6500" by NIR Systems Inc. Generally known reflectance spectrophotometers comprise a cell or container within which a sample of the material for analysis is retained; a source providing a beam of electro-magnetic radiation (usually near infrared as previously mentioned) which is applied to the material in the cell, and sensors or detectors which are responsive to reflections from the material in the cell and provide an output from which the analysis is effected. Usually the spectrophotometer is coupled to a computer by which the application of the beam to the material is controlled and which provides a required analysis of the output from the sensors or detectors.

A particular concern when using reflectance spectrophotometers is to ensure that stray electromagnetic radiation reflected back to the sensors or detectors is minimised. Understandably such stray or spurious reflections from parts of the spectrophotometer apparatus to which the beam may be applied will be presented for analysis along with the intended reflections from the sample material and thus result in false or inaccurate measurements. Where relatively large volumes of material are available for spectrophotometric analysis so that such material may be presented in a sample cell or container distributed over a relatively large area which is subjected to the beam, the stray light reflectance may be regarded as insignificant in assessing the accuracy of the analysis measurements. However, when only a relatively small volume of sample material is available or desired for analysis there is a problem that spurious or stray light reflections can have a significant adverse effect on the accuracy of the analysis measurements—this problem frequently occurs in the pharmaceutical industry (where it is quite common for only a very small volume of highly expensive pharmaceutical to be made available for spectrophotometric analysis). It is an object of the present invention to provide an apparatus for reflectance spectrophotometric analysis by which the aforementioned problem may be alleviated. It is also an object of the present invention to provide an apparatus in the form of a conversion kit by which conventional reflectance spectrophotometers may be converted in a relatively simple, efficient and economic manner for use with a cell or container for a relatively small sample of material that is to be subjected to analysis and which conversion alleviates the aforementioned problem of stray or spurious reflections from the electromagnetic beam from being applied to the sensors or detectors.

STATEMENTS OF INVENTION AND ADVANTAGES

According to the present invention there is provided apparatus for spectrophotometric analysis of a material by reflectance measurements resulting from a beam of electromagnetic radiation applied to the material which comprises a station at which a container housing the material is to be located, a primary mask having an aperture through which the beam is to be directed to the station and which aperture forms a restriction to provide a beam of predetermined cross section, and a secondary mask which is substantially non-reflective to the electromagnetic radiation and is interposed between the primary mask and the station, said secondary mask having a port through which the restricted beam is to be directed to the station, the primary mask and secondary mask being arranged so that the restricted beam is accommodated substantially wholly within the port for its application to the material and wherein reflected electromagnetic radiation from the material subjected to the restricted beam is detected for analysis measurement from such reflected radiation passing through the port of the secondary mask.

Usually the electromagnetic beam will be visible light or near infrared light and for convenience the latter will hereinafter be referred to. By the present invention it is intended that the aperture of the primary mask will provide a light beam of predetermined cross section and direct this beam wholly, or substantially so, into the port of the secondary mask through which the light beam is to be applied to the material or substance under analysis. The secondary mask is substantially non-reflective to the light beam to alleviate stray light from being reflected from the secondary mask to the sensors or detectors of the spectrophotometer in the event that a peripheral part of the beam should inadvertently be mis-directed to strike the secondary mask. The principle purpose of the secondary mask is to define by its port what may be a relatively small target area through which the sample material for analysis is subjected to (or illuminated by) the light beam and also through which port reflected light is made available to the detectors or sensors for analysis purposes. By having a relatively small area port in the secondary mask, it is possible for the port to be covered fully by the sample material even though only a relatively small volume of such material may be available or desirable. With this in mind, the station at which the container of sample material is to be located preferably comprises a seating in which the container is to be accommodated and retained in a predetermined position for the sample material to overlie fully the port in the secondary mask. Consequently, with the light beam being directed wholly through the port in the secondary mask and such port being covered fully by the sample material, it will be appreciated that the reflected light will emanate wholly or substantially so from the sample material. The seating for the container or cell is conveniently provided in a holding block with the secondary mask being disposed between the holding block and the primary mask. Indeed the holding block may be formed integral with the secondary mask.

Whilst the primary mask and secondary mask are matched to each other in a sense that the aperture and port thereof are sized, shaped and positioned so that the light beam from the aperture is directed wholly within the port, it is not essential that the cross section of the light beam where it illuminates the port corresponds exactly with the cross section of the port. In fact in practice it will be usual for the aperture of the primary mask to restrict the beam cross section so that it illuminates the port over an area less than that of the port and for the restricted beam from the aperture to be accommodated wholly within the port of the secondary mask substantially centrally of that port. Typically the port of the secondary mask will be circular whilst the aperture of the primary mask will provide a restricted beam of rectangular cross section to provide illumination within the circular port.

Conventional reflectance spectrophotometers present the light beam to the sample material for analysis by way of a translucent sheet window (typically of optical quartz) and light reflected from the sample is redirected through the window to the sensors or detectors. With such apparatus it is preferred that the sheet of the window is disposed between the primary mask and the secondary mask.

The apparatus of the present invention is also provided in combination with a container or cell within which the material for analysis is accommodated. The container is preferably located at the station for the material therein to overlie the port and extend beyond the whole periphery of that port in the secondary mask. The secondary mask can consequently serve to prevent the light beam which is directed through the port from being applied directly to peripheral parts of the container which could otherwise develop spurious light reflections and adversely affect the accuracy of the spectrophotometric readings. Usually the container will have a substantially flat wall part which fully overlies the port and extends beyond the whole periphery of that port and through which wall part the restricted light beam is directed to the sample material extending over the wall part. This wall part is conveniently arranged to abut the secondary mask to overlie its port. In fact, where the spectrophotometer includes a sheet window as aforementioned, the secondary mask conveniently serves to protect the window from being damaged by the container, for example by preventing the container from scratching the surface of the window. The previously mentioned seating for the container at the station will usually be sized and profiled to accommodate a predetermined size and shape of container to retain that container in a predetermined position over the port of the secondary mask. A preferred form of container is a conventional vial as typically used for housing pharmaceutical samples and having a substantially circular flat base and a substantially cylindrical side wall extending concentrically from the base; usually the restricted light beam and reflected light will be directed to and from the sample material in the vial through the flat base. Preferably the vial will be located in a seating or otherwise at the station to ensure that its base fully overlies the port of the secondary mask whilst the whole periphery of the base (comprising its junction with the cylindrical side wall) is located wholly outside the periphery of the port to ensure that the restricted light beam from the primary mask is applied to illuminate the sample material in the vial through the vial base otherwise than through the vial base at its junction with the side wall. The port in the secondary mask can consequently serve to define or isolate for the restricted light beam a predetermined target area on the base of the vial remote from the peripheral junction of the base with the vial side wall over which the sample material is disposed to be subjected to the restricted light beam. It has been determined that should the restricted light beam be applied through the port of the secondary mask to illuminate the base of the vial at its peripheral junction with the vial side wall spurious light reflections and refractions can develop which adversely affect to a substantial extent the accuracy of the spectrophotometric readings which result from the reflected light.

It is preferred that the light beam passing through the aperture of the primary mask and port of the secondary mask is directed substantially vertically. The reason for this preference is that when the sample material for analysis is a powder, it permits the powder to be uniformly dispersed over a substantially horizontal wall of the container through which the vertical light beam is applied to the material. It will be appreciated however that the present invention may be applied to spectrophotometers in which the light beam is directed other than vertically.

The apparatus of the present invention may be utilised for analysis of sample material in liquid form. With liquid samples it is preferred that the container is elongated and retained by the aforementioned seating at the station so that the axis of the container over its elongated extent is other than horizontal; this is to ensure that any gas bubble which may be present in the liquid sample will be displaced to an upper end of the container and thereby remote from the part of the liquid sample that may be subjected to the restricted light beam applied thereto through the port of the secondary mask. Typically such an elongated container will be in the form of a vial or test tube which is substantially cylindrical about, and concentric with, its elongated axis and retained in the seating with its axis inclined to the horizontal so that any gas bubble in the liquid sample will be displaced to the upper end of the container to ensure that the gas bubble is not within a target region of the liquid sample (as defined by the port of the secondary mask) as such a gas bubble in the incident light beam or reflected light can adversely affect the accuracy of the spectrophotometric measurements.

The station of the apparatus can include a surface reflective to the light beam. This reflective surface is located so that the container can be disposed between it and the port of the secondary mask whereby the restricted beam from the port, if passing through or by the container and sample material therein, can be reflected from the reflective surface back towards the port of the secondary mask to be applied to the sensors or detectors. Understandably such a reflective surface, if provided, may be superfluous where the sample of material for analysis fully covers the port of the secondary mask and is of sufficient depth or opaquity so that it is not penetrated by the light beam. Usually the reflective surface will be provided when analysing a liquid sample housed in an inclined container as previously described where it is possible that the light beam will be refracted through the cylindrical wall of the container and possibly pass through the liquid sample to be reflected from the reflective surface back towards the detectors.

To facilitate individual spectrophotometric analysis of numerous samples of the same or different materials in a convenient and efficient manner, the apparatus of the present invention may include means for carrying an array of containers, for feeding each container successively to locate it at the station for spectrophotometric measurement of its sample material contents and for removing the respective container from the station following such measurement. Desirably the feed and removal of the containers to/from the station at which the measurements are taken is effected automatically under computer control, such computer conveniently being programmed to effect the required spectrophotometric measurements. The means for carrying, feeding and removing the array of containers is conveniently in the form of an endless conveyor such as a carousel, intermittent displacement or rotation of which feeds each container successively to the station, retains the respective container stationary at the station for spectrophotometric measurement of its sample contents and following such measurement displaces or rotates to remove the respective container from the station.

The present invention was primarily developed to alleviate the problems as previously mentioned resulting from spurious or stray light reflections associated with conventional reflectance spectrophotometers and with this in mind it was an aim to provide a means whereby such conventional spectrophotometers could be modified in a convenient, simple and relatively inexpensive manner to provide the apparatus of the present invention. To satisfy the aforementioned aim, there is further provided a conversion kit for a spectrophotometer providing analysis of a material by reflectance measurements resulting from a beam of electromagnetic radiation applied to the material through a translucent sheet window thereof and which kit comprises a primary mask having an aperture and which is to be fitted to the spectrophotometer for said aperture to restrict the beam directed through the window to a predetermined cross section; a secondary mask which is substantially non-reflective to the electromagnetic radiation and having a port and which secondary mask is to be fitted to the spectrophotometer on the side of the window remote from the mask for the restricted beam passing through the window to be directed substantially wholly within the port, and means for locating a container housing the material on the side of said secondary mask remote from the window for said restricted beam passing through the port to be applied to the material in the container and for reflected electromagnetic radiation from the material which is subjected to the restricted beam to be directed through the port and window for analysis measurement.

The conversion kit will be intended for a particular make and model of reflectance spectrophotometer so that the primary mask may easily be fitted in the apparatus by simply removing the sheet window thereof, securing the primary mask over the light source slit, refitting the window and securing the secondary mask to overlie the window on the side of that window remote from the primary mask and then fitting to or over the secondary mask the means (such as a seating) for locating the container to overlie the port of the secondary mask (assuming that such means or seating is not formed integral with the secondary mask). It will, of course, be appreciated that the primary and secondary masks will be matched to each other as previously discussed and as appropriate for a particular make and model of reflectance spectrophotometer. Therefore the size and shape of the respective aperture and port and the positioning and spacing of the masks as fitted will vary accordingly.

DRAWINGS

One embodiment of apparatus for spectrophotometric analysis constructed in accordance with the present invention will now be described, by way of example only, with reference to the accompanying illustrative drawings in which.

DETAILED DESCRIPTION OF DRAWINGS

Figure 1:
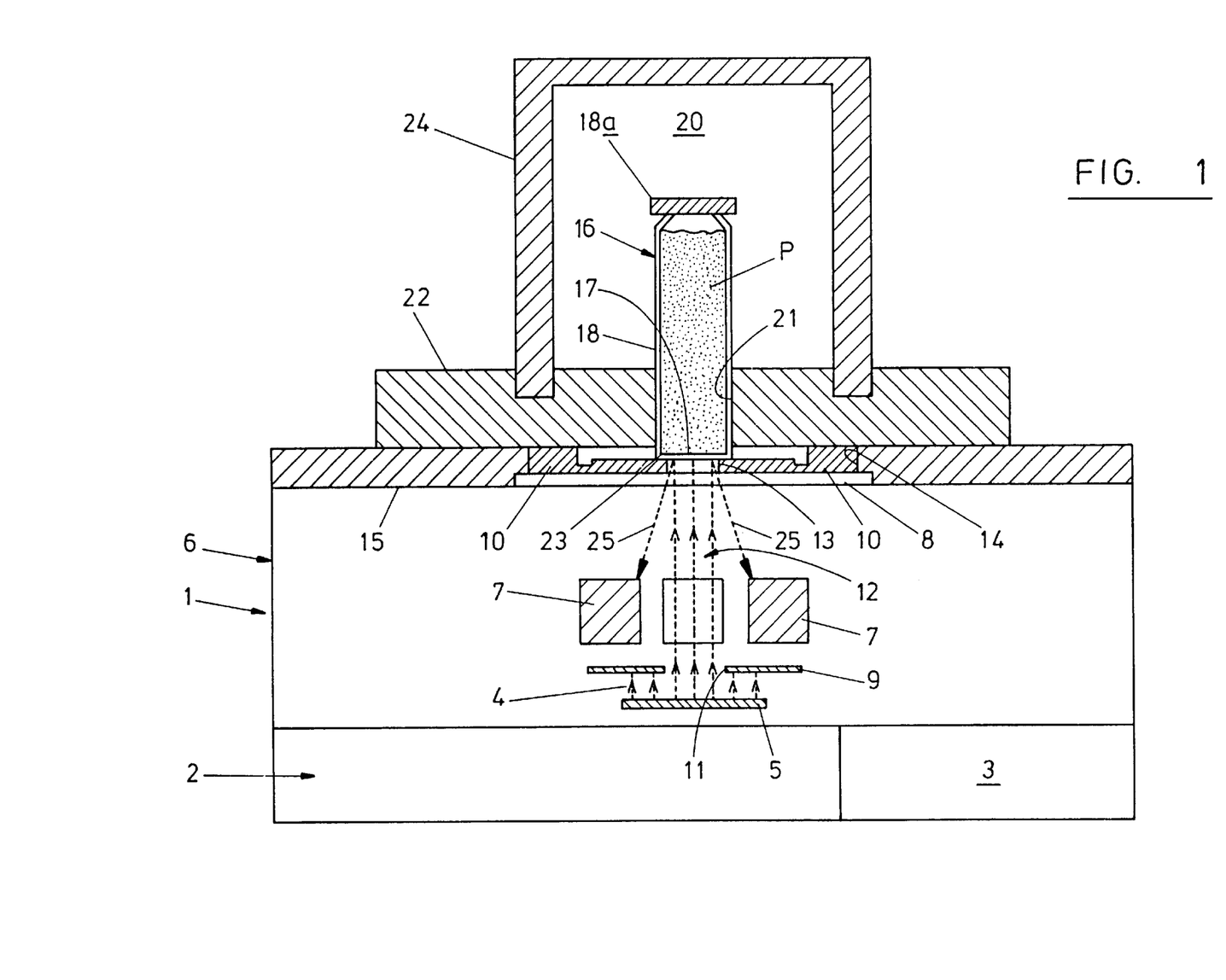
FIG. 1 diagrammatically illustrates a section in side elevation through a module part of the apparatus intended for use in the analysis of a sample material retained in a vial and particularly shows the primary and secondary masks.

The apparatus shown diagrammatically in FIG. 1 includes a spectrophotometer unit 1 for analysis of a sample material by reflectance measurements from a beam of near infrared light that is applied to the sample. The unit 1 is, conveniently, predominantly comprised of a generally known spectrophotometer unit, for example that as sold under the Trade Mark MODEL 6500 by NIR Systems Inc. Such a known spectrophotometer has a monochromator part 2 which is usually coupled to a computer 3 (not normally regarded as part of the spectrophotometer) from which it receives commands and transmits data back for analysis purposes. The function of the monochromator 2 is well known in the art and includes the generation of monochromatic near infrared light 4 which it presents through a slit 5. Coupled to the monochromator 2 and forming part of the spectrophotometer is a reflectance module 6 into which the near infrared light 4 is presented from the slit 5. Conventionally included in the module 6 are sensors or detectors 7 which are responsive to near infrared light and when subjected to such light transmit signals to the monochromator 2 and therethrough data to the computer 3 for analysis measurements to be effected. In a conventional spectrophotometer light 4 from the slit 5 is directed through a flat optical quartz window 8 in a base plate 15 of the module 6 onto a sample material for spectrophotometric analysis located at a scanning station 20. This sample material is housed in a cell or other container which stands on the window 8 externally of the module 6 so that light reflected from the sample material re-enters the module 6 through the window 8 to be picked up by the detectors 7 for effecting the analysis.

Figure 1A:
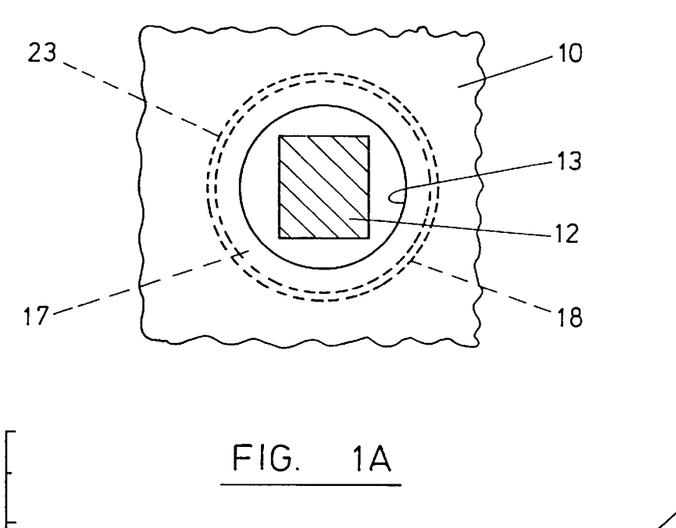
FIG. 1A is a scrap plan view of part of the apparatus in FIG. 1 and illustrates the illumination of the port in the secondary mask by the light beam.

The present invention is primarily concerned with the module 6 in so far as it is provided with a primary mask 9 and a secondary mask 10. The primary mask 9 is fitted and secured adjacent to the light slit 5 and has a rectangular aperture 11. The primary mask 9 is opaque and preferably substantially non reflective to the near infrared light 4 and serves to restrict that light to a beam 12 of rectangular cross section which passes through the aperture 11 to be directed through the glass window 8 perpendicularly to the plane of that window. The secondary mask 10 is non-reflective and opaque to near infrared light and includes a circular port 13. The mask 10 is mounted in face-to-face contact with the glass window 8 and is removably retained in a recess 14 of the base plate 15 which carries the glass 8. The secondary mask 10 is located so that its port 13 is in direct alignment with the beam 12 emanating from the aperture 11. Furthermore, the aperture 11 and port 13 are matched in so far as the rectangular sectioned beam 12 which emanates from the aperture 11 illuminates and falls wholly within the port 13 substantially centrally of that port (this is best seen in FIG. 1A). By this latter arrangement it will be appreciated that negligible, if any, light from the beam 12 will be reflected to the detectors 7 from the mask 10.

The apparatus shown in FIGS. 1 and 1A is primarily intended for spectrophotometric analysis of pharmaceutical samples where such samples may be available only in small quantities. In FIG. 1 such a sample P in powder form is housed within a conventional pharmaceutical thin walled glass vial 16 having a flat circular base 17 and an open topped cylindrical side wall 18 upstanding from the base to be concentric therewith and closed by a cap or stopper 18a.

The vial 16 is located at the scanning station 20 on the module 6 so that its circular base 17 overlies and is concentric with the port 13 of the secondary mask. For the purpose of locating the vial 16 correctly on the mask 10, the cylindrical wall 18 of the vial is slidably accommodated in a seating formed by a complementary cylindrical bore 21 in a holding block 22 removably mounted on the base plate 15 of the module. From FIGS. 1 and 1A it will be seen that the diameter of the port 13 is considerably less than the diameter of the vial base 17 and is also less than the internal diameter of the vial at its base 17. Consequently when the vial base 17 is concentric with the port 13, the marginal periphery of the vial base which includes the junction between that base and the side wall 18 (which junction is illustrated at 23 in FIG. 1A) does not overlie the port 13 and is therefore remote from the incident beam 12. A conventional pharmaceutical vial will have a base diameter not greater than 20 millimetres and a thickness for its cylindrical wall not greater than 2 millimetres, typically the vial base diameter will be 15 millimetres, the cylindrical wall thickness will be 0.5 millimetres and the vial will have a capacity in the order of 4.0 ccs. With such a typical vial the port 13 may have a diameter of, say, 12 millimetres whilst the primary mask 9 restricts the near infrared light 4 so that the beam 12 emanating from the aperture 11 has a rectangular cross section (which illuminates the port 13 as shown in FIG. 1A) of, say, 10 millimetres by 6 millimetres.

The vial 16 at the station 20 is enclosed within an opaque casing 24 removably mounted on the holding block 22.

With the beam 12 directed substantially vertically (as is preferred) the sample powder P will be dispersed uniformly over the vial base 17 fully over and beyond the whole periphery of the port 13. As a consequence the beam 12 directed through the port 13 will be applied to the powder P for light 25 reflected therefrom to be applied to the detectors 7 for spectrophotometric analysis in conventional manner. In particular, it will be noted that the periphery of the vial base which includes the annular junction 23 between that base and a cylindrical side wall 18 is blocked by the secondary mask 10 against any light being applied directly to that junction from the beam 12. This alleviates spurious or stray light reflections which could otherwise emanate from the wall/base junction 23 of the vial from adversely affecting the accuracy of the spectrophotometric measurements. Where the cross section of the beam 12 which illuminates the port 13 does not correspond with and is less than the area of the port 13 in the secondary mask (so that part of the area of the port 13 is not illuminated by the beam 12 as will be seen from FIG. 1A) it has been found that this lack of illumination has negligible effect on the accuracy of the spectrophotometric measurements—this is believed to be due to the fact that the incident light 12 which is directed to the sample powder P and reflected therefrom is scattered by the powder and can return to the detectors 7 through the non-illuminated part area of the port 13 to provide useful light for the analysis measurements. It will be appreciated however that the shape and relative proportion of the area of the port 13 which is illuminated by the beam 12 can be altered as required simply by changing either or both of the masks 9 and 10 to change the size/configuration of the aperture 11 and/or port 13.

The holding block 22 and secondary mask 10 may be integral. It is preferred however that they are separate components so that different holding blocks can be applied to the same secondary mask 10 (such different holding blocks having different diameter seatings 21 for accommodating differently sized vials 16). Also by having the holding block 22 removable, a reference standard material (for example "Spectralon"—Trade Mark) may be fitted directly over the port 13 for the purpose of providing a standard approximately 99% reflective surface to the near infrared light from the beam 12 in setting up the spectrophotometer prior to carrying out an analysis measurement.

It will be seen from FIG. 1 that the base 17 of the vial 16 stands on and is in face-to-face contact with the secondary mask 10 so that the beam 12 immediately enters the base of the vial from the port 13. Furthermore, the secondary mask 10 (which like the primary mask 9 and block 22 will usually be formed of metal plate) serves to protect the outer surface of the glass window 8 from being damaged, for example scratched, by contact with the vial base.

It will be apparent to those skilled in the art and having an understanding of the present invention that the light slit 5, detectors 7 and window 8 in the base plate 15 of the module 6 are conventional for many known reflectance spectrophotometers. Consequently, for a given make and model of such known spectrophotometers the present invention lends itself to the provision of a conversion kit (comprising the primary mask 9, secondary mask 10, holding block 22 and cover 24) which is specifically designed to be fitted to a reflectance module 6 of such a particular known spectrophotometer and which conversion fitting can readily be effected by a laboratory technician.

Figure 2:
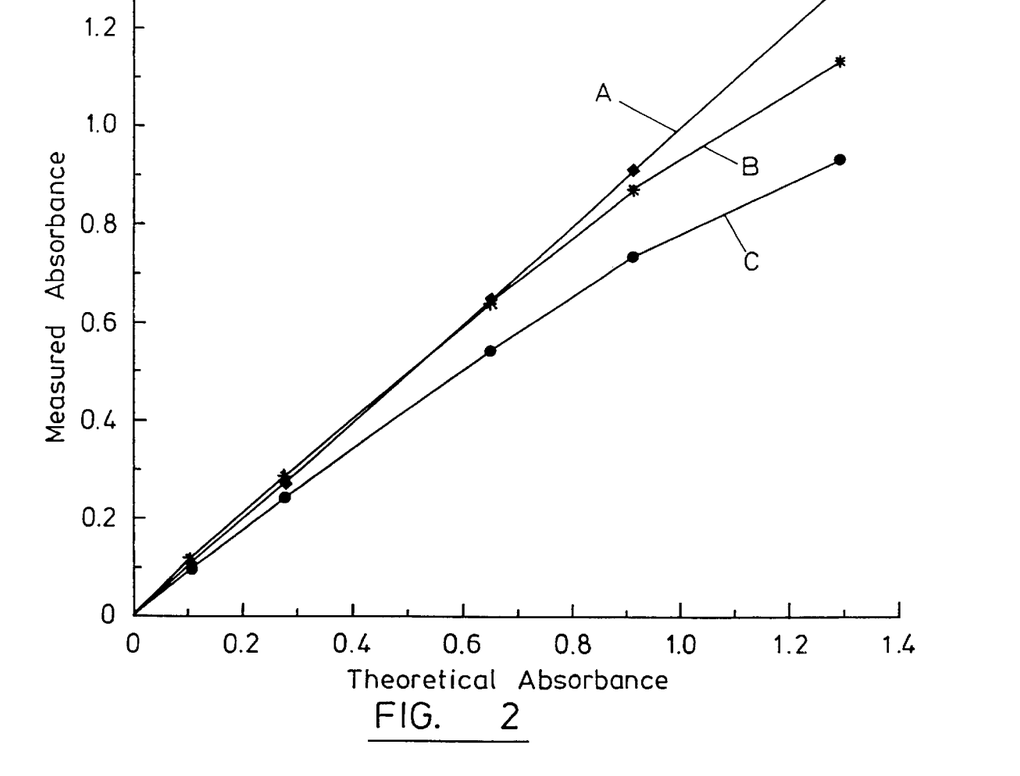
FIG. 2 shows graphs comparing Measured Absorbance with Theoretical Absorbance determined from the apparatus of FIG. 1 and compares measurements from such apparatus with and without the masks.

The primary purpose of the apparatus shown in FIG. 1 is to alleviate spurious or stray reflected light from being applied to the detectors 7 during spectrophotometric analysis and the advantageous effect of such apparatus can readily be appreciated from the graphs shown in FIG. 2. In FIG. 2 the ordinate shows Measured Absorbance of near infrared light by a particular sample material whilst the abscissa shows the Theoretical Absorbance of the near infrared light by that sample. The graphs are derived using a range of "Spectralon" (Trade Mark) standards at 1800 nm, relative to a 99% reflective Spectralon standard. It is known that absorbance (A) is measured according to the following equation:

$$A = -\log((I+I_s)/(I_o+I_s))$$

where I is the intensity of light reflected from a sample under test, Io is the intensity of light reflected from the 99% Spectralon standard and Is is the intensity of the stray radiation. As the reflectivity of the sample decreases the effect of the Is term becomes increasingly significant. Restricting the amount of light falling on the secondary mask by directing the restricted beam wholly through the port 13 onto the sample decreases the magnitude of the Is term. This increases the linear dynamic range of the near infrared spectrophotometer and improves the spectra acquired from it and thereby the quality of the analysis. In FIG. 2 graph A is the theoretical absorbance of the particular sample. Graph B plots the measured absorbance with theoretical absorbance of the sample with the apparatus as shown in FIG. 1 where it will be seen that up to approximately 1.0 absorbance units the measured absorbance is little, if any, different from the theoretical absorbance. Graph C plots the measured absorbance to the theoretical absorbance for the sample using the apparatus substantially as in FIG. 1 but with the primary and secondary masks 9, 10 removed—here it will be seen that the measured absorbance rapidly diverges from the theoretical absorbance to the extent that the measurements indicate far less light had been absorbed by the sample than was in fact absorbed (due to the stray reflected light being picked up by the detectors in addition to the useful reflected light). For typical pharmaceutical samples the absorbance range of interest is between 0.2 to 0.8 absorbance units and it will be seen from the graphs that within this range the Graph B for the apparatus shown in FIG. 1 provides an extremely accurate measured absorbance (unlike Graph C derived from the apparatus without the primary and secondary masks).

Figure 3:
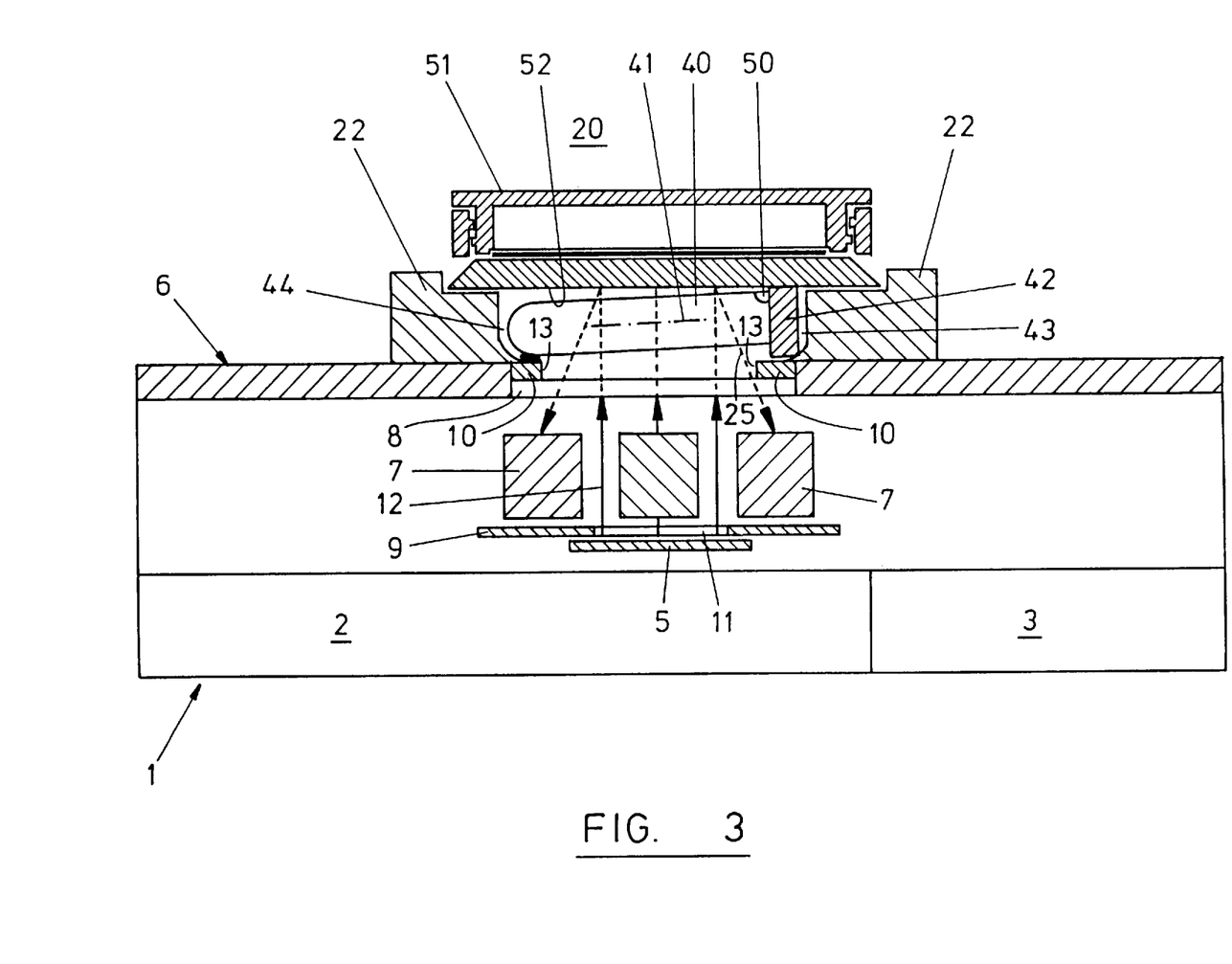
FIG. 3 is a section of apparatus similar to that shown in FIG. 1 and diagrammatically illustrates a modification to provide a seating of the apparatus suitable for retaining a container housing a liquid sample for analysis.

The modification shown in FIG. 3 is primarily intended for use with analysis of a sample material in liquid form which is housed in an elongated vial or tube 40 of cylindrical form having a longitudinal axis 41. The sample is sealed in the vial by a cap 42. The holding block 22 is modified to present longitudinally spaced seatings 43, 44 within which longitudinally opposed ends of the vial 40 are received to retain the vial so that its mid-part length bridges the port 13 of the secondary mask 10. It will be noted from FIG. 3 that the port 13 is considerably wider than that shown in FIG. 1 and unlike the circular port 13 in FIG. 1, the port in FIG. 3 may be an oblong rectangle to conform with the major mid-part length of the vial 40. However, it will also be seen from FIG. 3 that the longitudinally opposed ends of the vial 40 overlie the secondary mask 10 so that those ends are blocked by the secondary mask 10 from having near infrared light applied directly thereto from the team 12 (which beam is restricted by the primary mask 9 to be applied to the mid-length region of the vial 40 wholly through the port 13).

From FIG. 3 it will be seen that with the beam 12 being directed vertically, the vial 40 is mounted by the seatings 43 and 44 in the holding block 42 so that its longitudinal axis 41 is inclined to the horizontal. The effect of this is that should a gas bubble be present in the liquid sample, such bubble (as indicated at 50) will be displaced to the upper end of the vial 40 and thereby to a position remote from the incident beam 12—by this technique a bubble in the sample material is unlikely to affect the reflectance measurements. A further modification in FIG. 3 is that the holding block 22 carries a "Spectralon" (Trade Mark) 51. This has a standard light reflective surface 52 that provides approximately 99% efficiency in the reflection of near infrared light. The "Spectralon" (Trade Mark) surface 52 provides a backing for the vial 40 so that the latter is disposed between that surface 52 and the secondary mask 10. With many liquid samples it is likely that the incident beam 12 will pass through the vial 40 and its sample to be reflected from the surface 52 back through the vial to the detectors 7. It is also possible for the vial to present a smaller target area than the area of the port 13 illuminated by the beam so that light from the beam 12 may be applied directly to the surface 52 to be reflected towards the detectors 7; however provided that the same conditions are maintained for all of the spectrophotometric measurements, should light be applied directly to the surface 52 and reflected therefrom directly back to the detectors 7 the sample analysis should not be adversely affected. The primary advantages derived from the arrangement shown in FIG. 3 are that the secondary mask 10 alleviates the likelihood of spurious or stray light reflections emanating from the ends of the vial 40 (particularly that end having the cap 42), and that an air bubble if present in the liquid sample will be displaced naturally away from the region of the sample which is illuminated by the incident beam 12. A further advantage derived from the arrangement of FIG. 3 is that the cylindrical wall of the vial 40 serves to provide light refraction through the sample material which it is believed improves the quality of the analysis measurements.

Figure 4:
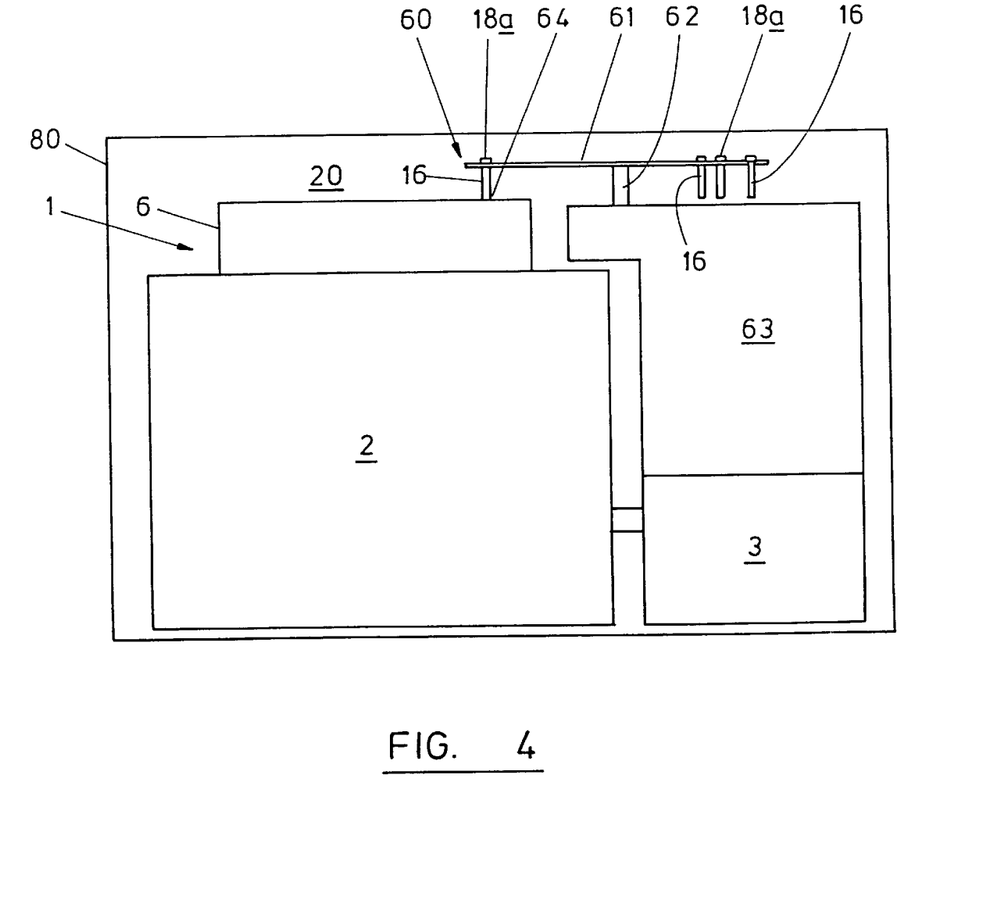
FIGS. 4 and 5 are side and plan views respectively diagrammatically illustrating a modification of the apparatus shown in FIG. 1 for sequential and automatic spectrophotometric analysis of samples of material carried in an array of containers.
Figure 5:
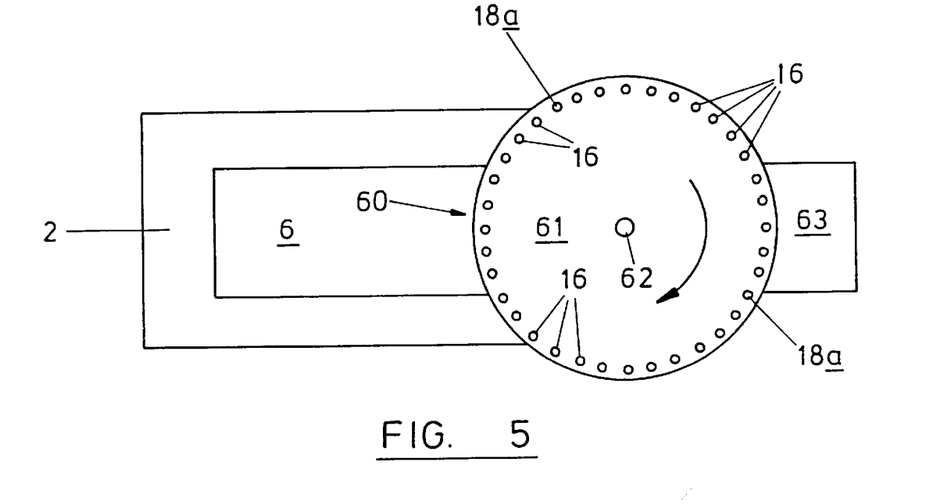
Figure 6:
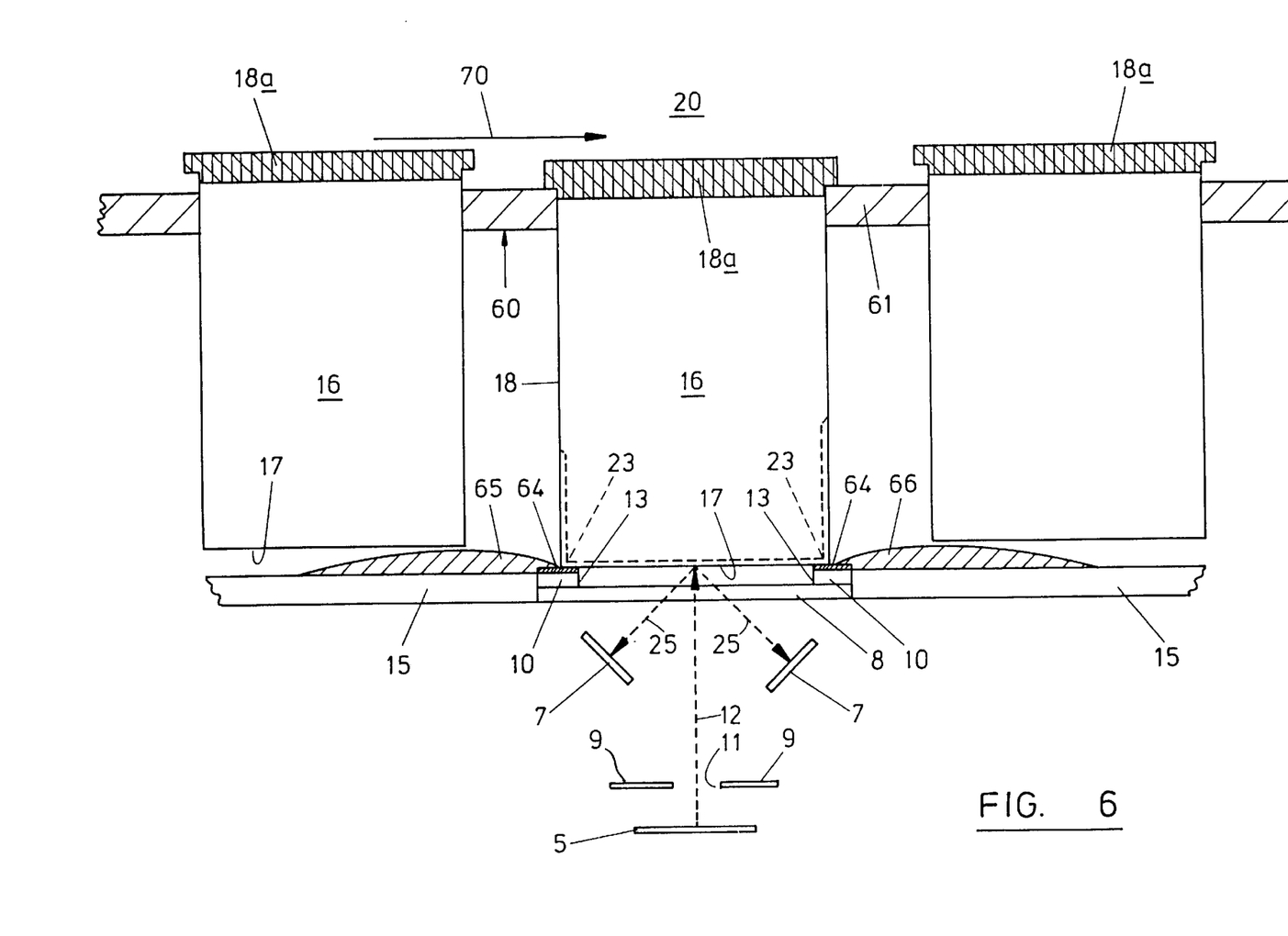
FIG. 6 is an enlarged side view of part of the apparatus shown in FIG. 4 and illustrates the manner in which each container of the array is presented for analysis of its contents.

The apparatus shown in FIGS. 4 to 6 includes a modification from that shown in FIG. 1 whereby an array of vials 16 each containing sample material for analysis are fed successively and automatically to the scanning station 20 for spectrophotometric analysis of the respective samples and removed from the station following such measurement. The modification includes an endless conveyor in the form of a carousel 60 comprising a substantially horizontal circular disc 61 centrally mounted for rotation on a vertical shaft 62 which is coupled to be rotated by a drive unit 63.

The vials 16 containing the samples for analysis are disposed in a circumferentially spaced array at the marginal peripheral edge part of the disc 61 (as best seen in FIG. 5). Each vial is received as a free sliding fit in an aperture in the disc 61 and is suspended from the disc by abutment of its cap 18A with the upper surface of the disc. For convenience not all of the suspended vials 16 have been shown in FIG. 4. The drive unit 63 is controlled automatically by the computer 3 in synchronisation with actuation of the spectrophotometer 1 to rotate the shaft 62 and thereby the disc 61 intermittently to feed the vials 16 successively to the station 20. For the purpose of receiving the successive vials the station 20 is modified from that shown in FIG. 1 and includes an annular vial seating 64 on the secondary mask 10 concentric with its circular port 13 and which seating 64 is disposed between ramps 65 and 66 on the base plate 15. The ramps 65 and 66 are located beneath the circular path along which the vials are carried by the rotating carousel and lead and trail respectively relative to the direction of movement of the vials during rotation of the disc 61 (in the direction of arrow 70). The ramps 65 and 66 are conveniently coated with a low friction material such as pplytetrafluoroethylene and are arranged together with the vials on the carousel so that as the disc 61 is rotated, the base 17 of a vial approaching the station 20 will abut and slide over the leading ramp 65 causing that vial to be displaced vertically upwardly relative to the disc 61 so that it is no longer suspended by its cap 18A from the disc. Further rotation of the carousel displaces the vial from the leading ramp 65 into the seating 64 at which position the vial is displaced downwardly under gravity to stand on the secondary mask 10 and at the location determined by the seating 64 to be concentric with the port 13. In this condition and with the carousel stationary the spectrophotometer is actuated to effect the analysis measurements. Following such measurements the disc 61 is further rotated to displace the vial 16 from the seating 64 into abutment with the trailing ramp 66 which ramp causes the vial to be raised from the seating 64 so that the vial slides over the ramp 66 to clear the station 20 and eventually drops relative to the disc 61 to be suspended from the disc by its cap 18A. The automatic intermittent rotation of the disc 61 under control of the computer 3 ensures that the feed of the vials 16 to the seating 64 is synchronised with the analysis measurements which are effected on the vial that is stationary on the seating 64.

Desirably the station 20 together with the carousel and vials 16 carried thereby are enclosed within an opaque cover 80.

We claim:

1. Apparatus for spectrophotometric analysis of a material by reflectance measurements resulting from a beam of electromagnetic radiation applied to the material which comprises a station at which a container housing the material is to be located, a primary mask having an aperture through which the beam is to be directed to the station and which aperture forms a restriction to provide a beam of predetermined cross section, and a secondary mask which is substantially non-reflective to the electromagnetic radiation and is interposed between the primary mask and the station, said secondary mask having a port through which the restricted beam is to be directed to the station, the primary mask and secondary mask being arranged so that the restricted beam is accommodated substantially wholly within the port for its application to the material and wherein reflected electromagnetic radiation from the material subjected to the restricted beam is detected for analysis measurement from such reflected radiation passing through the port of the secondary mask.

2. Apparatus as claimed in claim 1 in which the station comprises a seating in which said container is to be accommodated and retained in a predetermined position for the material therein to overlie fully the port.

3. Apparatus as claimed in claim 2 in which the seating is provided in a holding block, said secondary mask being disposed between the holding block and the primary mask.

4. Apparatus as claimed in claim 1 in which the aperture of the primary mask restricts the beam cross section to an area less than that of the port and said restricted beam is accommodated wholly within the port substantially centrally thereof.

5. Apparatus as claimed in claim 1 in which the port of the secondary mask is substantially circular.

6. Apparatus as claimed in claim 1 in which the aperture of the primary mask provides a restricted beam of substantially rectangular cross section.

7. Apparatus as claimed in claim 1 in which a sheet window is disposed between the primary mask and the secondary mask and said restricted beam is directed through the window to the port and said reflected radiation is directed from the port through the window for detection and analysis.

8. Apparatus as claimed in claim 1 in combination with a container within which the material for analysis is accommodated.

9. Apparatus as claimed in claim 8 in which the container is located at the station for the material therein to fully overlie the port and extend beyond the periphery of that port.

10. Apparatus as claimed in claim 9 in which the container has a substantially flat wall part which fully overlies the port and extends beyond the periphery of that port and through which wall part the restricted beam is directed to the material extending over that wall part.

11. Apparatus as claimed in claim 10 in which the wall part is in abutment with the secondary mask to overlie the port therein.

12. Apparatus as claimed in claim 11 in which a sheet window is disposed between the primary mask and the secondary mask and said restricted beam is directed through the window to the port and said reflected radiation is directed from the port through the window for detection and analysis and the secondary mask protects the window from abutment by the container.

13. Apparatus as claimed in claim 8 in which the container is a vial having a substantially circular flat base and a substantially cylindrical side wall extending concentrically from said base and said restricted beam and reflected electromagnetic radiation are directed to and from the material in the vial through the flat base.

14. Apparatus as claimed in claim 13 in which the station comprises a seating in which said container is to be accommodated and retained in a predetermined position for the material therein to overlie fully the port and the seating comprises a cylindrical opening in which the cylindrical side wall of the vial is received as a substantially complementary fit.

15. Apparatus as claimed in claim 13 in which the base of the vial fully overlies the port of the secondary mask so that the periphery of the base comprising its junction with the cylindrical side wall is located wholly outside the periphery of the port of the secondary mask whereby the restricted beam is applied to the material in the vial through the vial base and otherwise than at a position through the vial base at its junction with the side wall.

16. Apparatus as claimed in claim 13, in which the vial has a base diameter not greater than 20 millimetres and a wall thickness not greater than 2 millimetres.

17. Apparatus as claimed in claim 13 in which the port of the secondary mask is substantially circular and the circular base of the vial is substantially concentric with the port of the secondary mask.

18. Apparatus as claimed in claim 1 in which the restricted beam is directed substantially vertically.

19. Apparatus as claimed in claim 2 in combination with a container within which the material for analysis is accommodated in which the container is for liquid material and is elongated and retained by said seating so that its axis over its elongated extent is other than horizontal for displacing to an end of the container any gas bubble which may be present in the material so that such gas bubble is clear of the part of the material that is subjected to the restricted beam through the port.

20. Apparatus as claimed in claim 19 in which the container is substantially cylindrical about and concentric with its elongated axis.

21. Apparatus as claimed in claim 1 in which a surface reflective to the electromagnetic radiation is provided at said station, said surface being located so that the container can be disposed between it and the port for the restricted beam from the port, if passing through the container and material therein, to be reflected by the surface back towards the port.

22. Apparatus as claimed in claim 1 in which the station is enclosed by a removable opaque cover which is substantially non-reflective to the electromagnetic radiation.

23. Apparatus as claimed in claim 1 and comprising means for carrying an array of containers and feeding each container successively to locate it at said station for spectrophotometric measurements and removing the respective container from the station following said measurement.

24. Apparatus as claimed in claim 23 in which the feed and removal of the containers is controlled automatically by computer programmed to effect said spectrophotometric measurement.

25. Apparatus as claimed in claim 24 in which the means for carrying, feeding and removing the array of containers comprises a carousel, intermittent rotation of which feeds each container successively to the station, retains the respective container stationary at the station for spectrophotometric measurement and rotates to remove the respective container from the station following measurement.

26. Apparatus as claimed in claim 23 and comprising an opaque cover enclosing the station together with the means for carrying the array of containers and containers when carried thereby.

27. A computer when programmed to control the feed and removal of the containers for spectrophotometric measurement with the apparatus of claim 24.

28. A conversion kit for a spectrophotometer providing analysis of a material by reflectance measurements resulting from a beam of electromagnetic radiation applied to the material through a translucent sheet window thereof and which kit comprises a primary mask having an aperture and which is to be fitted to the spectrophotometer for said aperture to restrict the beam directed through the window to a predetermined cross section; a secondary mask which is substantially non-reflective to the electromagnetic radiation and having a port and which secondary mask is to be fitted to the spectrophotometer on the side of the window remote from the mask for the restricted beam passing through the window to be directed substantially wholly within the port, and means for locating a container housing the material on the side of said secondary mask remote from the window for said restricted beam passing through the port to be applied to the material in the container and for reflected electromagnetic radiation from the material which is subjected to the restricted beam to be directed through the port and window for analysis measurement.

* * * * *